US012605502B2

(12) United States Patent
   Deck

(10) Patent No.: US 12,605,502 B2
(45) Date of Patent: Apr. 21, 2026

(54) CRADLE FOR AN INFUSION PUMP UNIT

(71) Applicant: Roche Diabetes Care, Inc., Indianapolis, IN (US)

(72) Inventor: Frank Deck, Niederkirchen (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1116 days.

(21) Appl. No.: 17/369,665

(22) Filed: Jul. 7, 2021

(65) Prior Publication Data

US 2021/0330879 A1      Oct. 28, 2021

Related U.S. Application Data

(63) Continuation of application No. PCT/EP2020/050416, filed on Jan. 9, 2020.

(30) Foreign Application Priority Data

Jan. 11, 2019   (EP) .................................... 19151326

(51) Int. Cl.
   *A61M 5/142*        (2006.01)
   *A61M 5/162*        (2006.01)
(52) U.S. Cl.
   CPC ........ *A61M 5/14248* (2013.01); *A61M 5/162* (2013.01)
(58) Field of Classification Search
   CPC .............. A61M 5/14248; A61M 5/162; A61M 2005/14268; A61M 2039/1072; A61M 5/1413; A61M 39/10; A61M 2209/084;

A61M 2209/088; A61M 5/1424; A61M 5/14244; A61M 2005/14252; A61M 2005/14256; A61M 2005/1426; A61M 2005/14264

See application file for complete search history.

(56) References Cited

U.S. PATENT DOCUMENTS

2002/0084596 A1 * 7/2002 Michele ............... B41J 2/17513
                                                                277/609
2005/0065466 A1    3/2005 Vedrine
                    (Continued)

FOREIGN PATENT DOCUMENTS

CN      102186515 A      9/2011
CN      105935470 B     10/2020
                    (Continued)

OTHER PUBLICATIONS

International Search Report and Written Opinion of the International Searching Authority, PCT/EP2020/050416, Feb. 18, 2020, 9 pages.

*Primary Examiner* — Dung T Ulsh
*Assistant Examiner* — Fatimata Sahra Diop
(74) *Attorney, Agent, or Firm* — Bose McKinney & Evans LLP

(57)                      ABSTRACT

Disclosed is a cradle for an infusion pump unit. The cradle has a proximal side and a distal side, and the distal side has an infusion pump unit attachment structure for attaching an initially separate infusion pump unit. The cradle includes a cradle base, a flow channel for a liquid drug, and a pierceable septum. The pierceable septum covers an opening of the flow channel and seals the flow channel. An inner piercing core of the pierceable septum is movably mounted with respect to the cradle base.

25 Claims, 5 Drawing Sheets

(56)     References Cited

U.S. PATENT DOCUMENTS

| | | | |
|---|---|---|---|
| 2012/0203198 A1 | 8/2012 | Searle et al. | |
| 2012/0259185 A1* | 10/2012 | Yodfat | A61M 5/14244 |
| | | | 604/117 |
| 2013/0110049 A1* | 5/2013 | Cronenberg | A61M 5/1454 |
| | | | 604/239 |
| 2015/0057613 A1 | 2/2015 | Clemente et al. | |
| 2015/0157788 A1* | 6/2015 | Gescheit | G16H 20/17 |
| | | | 604/67 |
| 2019/0192841 A1* | 6/2019 | Lebau | A61M 39/04 |
| 2020/0324101 A1* | 10/2020 | Hartmann | A61M 39/105 |

FOREIGN PATENT DOCUMENTS

| | | | |
|---|---|---|---|
| JP | 2007-518455 A | 7/2007 | |
| JP | 2015-529501 A | 10/2015 | |
| JP | 2016-168411 A | 9/2016 | |
| JP | 2016-528017 A | 9/2016 | |
| JP | 2017-136270 A | 8/2017 | |
| WO | WO 2009/016635 A2 | 2/2009 | |
| WO | WO 2010/041261 A1 | 4/2010 | |
| WO | WO 2014/029416 A1 | 2/2014 | |
| WO | WO 2017/177094 A2 | 10/2017 | |
| WO | WO 2017/184801 A1 | 10/2017 | |

* cited by examiner

CRADLE FOR AN INFUSION PUMP UNIT

RELATED APPLICATIONS

This application is a continuation of PCT/EP2020/050416, filed Jan. 9, 2020, which claims priority to EP 19 151 326.6, filed Jan. 11, 2019, the entire disclosures of both of which are hereby incorporated herein by reference.

BACKGROUND

This disclosure lies in the field of cradles for infusion pump units and infusion systems including a cradle.

Continuous Subcutaneous Insulin Infusion (CSII) is an established and therapeutically advantageous way of treating diabetes mellitus. Under CSII, a diabetic carries a miniaturized infusion device in the form of an insulin pump substantially continuously, night and day. The insulin pump infuses metered quantities of insulin in a substantially continuous way according to a person-specific, generally time-variable infusion schedule or regime, thus providing a so-called basal amount of insulin that is required by the diabetic's body for maintaining a normal or close-to-normal metabolism and in particular blood glucose concentration. Typically, the basal administration schedule follows a generally circadian cycle and is pre-set by a healthcare professional. In addition, insulin pumps are designed to administer larger insulin quantities, so-called boli, within a short period of time on demand.

For a number of years, insulin pumps have virtually always been designed as battery-powered and self-contained devices with a footprint comparable to a credit card. This footprint allows them to be carried in a trousers' pocket, with a corresponding holster and a belt, as necklace, or the like. Via infusion tubing of typically 0.5 m to 1.5 m length, such devices are coupled to a subcutaneous infusion cannula. A typically syringe-like drug container that is received by a container compartment of the device as well as infusion tubing and the infusion cannula are designed as disposables and are replaced by the patient after a relatively short lifetime of typically a number of days. Over the last years, comparatively sophisticated devices have become available that may include wireless coupling to a remote controller, to a standard computer like a PC, a smartphone, or to glucose measurement devices or continuous glucose monitors (CGMs). A typical commercially available state-of-the-art system includes the ACCU-CHEK® Combo Spirit infusion device and the ACCU-CHEK® Combo Aviva remote controller and glucose measurement device, provided by Roche Diabetes Care.

Mainly in order to increase application comfort and discreetness, alternative devices and systems have been developed and have become available over the last years. Such devices, while operating according to the same technical principles, are designed as patch-devices that are adhesively attached directly to the infusion site. In addition, for eliminating the need of additional tubing between infusion device and infusion cannula, the infusion site—in most cases the abdomen region—is normally covered by cloths and therefore allows carrying the device in a particularly discrete way during most everyday life situations.

These devices are fully integrated disposable devices that need to be discarded and replaced once the application time, which is mainly determined by the container volume and the permissible indwelling time of the infusion cannula, has passed. Replacement is also required if the device is removed from the infusion site for further reasons, such as required for many sportive activities or showering.

For improving cost efficiency, modular patch-based systems have been designed that allow selective replacement of components. An example of such a system is disclosed in WO 2009/016635 A2, directed towards a system with a patch unit or liquid drug infusion device that is attachable to a cradle, with the cradle being removably attachable to a patient's skin. A subcutaneous infusion cannula is attached to the cradle and fluidic couples, in operation, to the patch unit. The patch unit may itself be two-parted and include a disposable drug container and a reusable dispensing mechanism and control circuitry. In addition to the general advantages associated with a modular design, the architecture allows temporary removing of the comparatively sensitive patch unit, including the drug container, e.g., for sportive activity, with the less critical and rugged cradle remaining attached to the skin.

In liquid drug infusion systems with a modular design, releasable fluid connections are often established by piercing a pierceable septum with a cannula, such as a transfer cannula. Such septa offer the advantage that complicated and expensive connecting members can be avoided. A septum is usually made from an elastic material such as rubber or silicone, which tightly seals a flow channel of a liquid drug. For connecting the flow channel with another device, for example an infusion pump unit, the septum is pierced by a transfer cannula upon which a piercing path is formed within the septum. Due to the radial force exerted by the cannula, the elastic septum material is pushed against the outer wall of the transfer cannula, resulting in a tight seal between the cannula and the septum. After disconnecting the cradle from the infusion pump unit, the piercing path is usually completely resealed due to the elastic characteristics of the septum. However, upon reconnection, i.e., upon an additional piercing event, a second puncturing path is generated, as the user typically cannot precisely identify and/or follow the previous puncturing path. Typically, the sealing property of the septum significantly decreases with every additional piercing event and the occurrence of leakage represents a severe problem.

Furthermore, the septum is typically not pierced in a straight manner and usually not perpendicular to the piercing surface of the septum. Perpendicular piercing is sometimes simply not possible, because the transfer cannula is manually introduced and the user cannot provide the required accuracy for piercing the septum. Furthermore, several devices have been developed which possess a relatively flat design in order to increase wearing comfort and decrease their visibility when attached to the patient's skin. In these devices, the septum may be pierced along a piercing path inclined with respect to the piercing surface of the septum. Piercing of a septum in such a manner entails deleterious effects on the sealing behaviour of the septum. For example, no radial symmetric force is exerted in these cases on the cannula, which decreases the sealing between the cannula and the septum. As a result, certain areas of the septum exhibit different forces than others, which may lead to areas being exposed to stretching effects and areas being exposed to compression effects. Additionally, a lateral force exerted by the cannula on the septum upon penetration may superimpose the radial symmetric force, which leads to an unsymmetrical pressure acting on the cannula. Furthermore, after removal of the cannula, optimal sealing of the puncture path can only be achieved if the septum is pierced in a strictly perpendicular manner and along a straight puncturing path.

In addition, due to design constraints, e.g., of a latching arrangement for infusion pump unit and cradle and/or due to the inaccuracy associated with manual, unguided piercing of the septum, the piercing event can be performed as a pivoting movement of the cannula. As a result, certain areas within the septum are stretched, while others are compressed by the pivoting piercing movement of the cannula. These stretching and compressing effects reduce the sealing behaviour of the septum and thus represent an additional source for leakage.

SUMMARY

This disclosure improves the state of the art regarding the design of cradles for infusion pumps in the context of infusion and/or injection of liquid drugs, thereby preferably avoiding disadvantages of the prior art fully or partly.

In favorable embodiments, a cradle is provided which guarantees that the septum is pierced perpendicularly to its piercing surface and/or that the septum is pierced along a straight puncturing path.

In further favorable embodiments, a cradle for an infusion pump unit is provided with an increased sealing behavior.

According to a first aspect of this disclosure, a cradle for an infusion pump unit is taught, wherein the cradle has a proximal side and a distal side. The distal side has an infusion pump unit attachment structure for attaching an initially separate infusion pump unit. The cradle comprises a cradle base, a flow channel for a liquid drug and a pierceable septum. The pierceable septum covers the opening of the flow channel and seals the flow channel in an uncoupled state of cradle and infusion pump unit. At least an inner piercing core of the pierceable septum is movable mounted with respect to the cradle base.

As used herein, the term "septum" is readily understood by those skilled in the art and is typically an engineered element, for example in the form of a membrane or plug, for sealingly separating a first side and second side in a fluid, i.e. gas and/or liquid tight seal, which can be pierced by a cannula. Typically, a septum does not comprise an opening or a puncture, which passes through the septum from the first side to the second side, before a cannula has been pierced through the septum. Consequently, a stump cannula cannot be easily pierced through the septum without exerting high forces. The septum thus seals the flow channel, however allows the penetration of a cannula for establishing a fluid connection.

Typically, the cradle base is rigid or essentially rigid and may be made from a plastic material. The cradle base has usually a flat, disk-like or elongated shape. Furthermore, the cradle base may be defined by a horizontal plane which comprises the disk-like or elongated shaped cradle base and which is in the operative state parallel to the patient's skin.

In typical embodiments, the flow channel of the cradle may be in fluid connection with a fluid connector, a tubing equipped with an infusion cannula or a tubing with a fluid connector. For example, such a connection may be established by a Luer connector or a suited proprietary fluid connector. In further embodiments, an infusion tubing is directly and permanently connected to the cradle base in fluidic coupling with the flow channel. In such embodiment, the tubing is an integral and inseparable part of the cradle.

The pierceable septum typically comprises an inner piercing core. While in some embodiments, the septum essentially consists of the inner piercing core, in other embodiments, the septum may comprise an inner piercing core and further parts, such as a sealing ring that surrounds the inner piercing core. However, in all embodiments, the inner piercing core of the septum is movably mounted with respect to the cradle base. It is understood that the term "movably mounted" refers to a movement in which the inner piercing core as a whole is moved. Thus, a local movement of only parts of the inner piercing core of the septum core does not represent a movement in this context. Therefore, at least the inner piercing core of the septum or also the pierceable septum as a whole is movably mounted with respect to the cradle base. As a consequence of this, any occurring asymmetric forces which may be exerted on the cannula upon piercing are avoided. Furthermore, the movable inner piercing core guarantees that the septum is pierced along a straight piercing path, thus providing a septum with an increased sealing behavior. Such a cradle additionally allows to increase the number of coupling and decoupling events of the cradle and an infusion pump unit.

In further embodiments, the proximal side has a skin attachment member for releasable attachment of the cradle to the patient's skin. The skin attachment member may for example be an adhesive strip, an adhesive layer, an adhesive patch or the like.

In some embodiments, the pierceable septum is sealingly connected to the cradle base by clamping or crimping. For example, the periphery of the septum may be heated, deformed and subsequently cooled while maintaining a crimping force. As a result, the septum may be prestressed, preferably radially prestressed with a force acting towards a central axis of the septum.

In some embodiments, at least the inner piercing core of the pierceable septum or also the pierceable septum as a whole is movable in a lateral direction of the cradle base and/or tiltable with respect to a horizontal plane of the cradle base. The horizontal plane of the cradle base is in the operative state essentially parallel to the patient's skin. Thus, in typical embodiments in which the cradle as a flat elongated or flat disk-like shape, the cradle is mainly arranged within the horizontal plane. The lateral direction is any direction within the horizontal plane. Typically, the lateral direction is in parallel to the piercing surface of the septum, i.e. the surface of the septum which is pierced upon establishing a fluid connection. Such embodiments are advantageous, as even in cases in which a cannula approaches the septum in an angle which is not strictly perpendicular to the piercing surface, the septum is tilted with respect to the horizontal plane of the cradle base when the transfer cannula of an infusion pump unit comes into contact with the piercing surface of the septum before the cannula penetrates the septum. For example, if the transfer cannula of a pump unit approaches the piercing surface of the septum in an angle of 60°, the septum tilts upon contact with the needle such that the piercing angle is essentially 90°, resulting in a straight piercing path. This ultimately increases the sealing behavior of the septum, as the forces exerted on the cannula upon piercing are radially symmetric.

In some embodiments the pierceable septum comprises a circumferential sealing ring, the inner piercing core and a deformable ribbon. The inner piercing core and the circumferential sealing ring are typically circumferentially connected by the deformable ribbon that is radially arranged between them. The ribbon is configured such that the inner piercing core of the septum is movable with respect to the cradle base and/or with respect to the sealing ring of the septum. Preferably, the deformable ribbon is configured such that the inner piercing core of the septum may be movable in a lateral direction of the cradle base and/or tiltable with respect to the horizontal plane of the cradle base. On the one hand, the ribbon may thus enable movement of the inner piercing core of the pierceable septum and on the other hand enables a gas and/or liquid tight septum sealing the flow channel of the cradle. The ribbon is usually thin, i.e. 0.1 to 5 mm, preferably 0.1 to 2.5 mm. Furthermore, the ribbon may be made from an elastomer or thermoplastic elastomer.

In typical embodiments, the circumferential sealing ring, the deformable ribbon and the inner piercing core of the pierceable septum are integrally formed. Usually, these are made from the same elastic material.

In such embodiments, it is preferable that the sealing ring, which surrounds the inner piercing core of the pierceable septum is connected to the cradle base by crimping or clamping. The foot print of the sealing ring and accordingly the overall footprint of the septum may be circular, but may also be shaped differently, such as rectangular, cuboid, triangular, pentagonal or hexagonal. In all embodiments, however, the sealing ring is circumferentially closed.

In some embodiments, the cradle comprises a stopper, wherein the stopper is configured to delimit a movement of the inner piercing core of the septum. Typically, the stopper is arranged below the septum. Thus, the stopper is arranged such that vertical movement of the inner piercing core is only allowed up to a predefined deflection with respect to a stress-free resting position. The stopper is usually designed such that a counterforce to the piercing force is provided. As a result, the inner piercing core is still movable or tiltable, however, the accuracy of the piercing is increased due to the exerted counterforce. Furthermore, rupture of the typically thin ribbon is prevented, which may be caused by excessive vertical deflection of the inner piercing core during a piercing event.

The stopper may for example be a broadening or a step within the flow channel, or a circular or rod-like support, a support lip within the flow channel or teeth protruding into the flow channel.

In some embodiments, the cradle comprises a pivotable arm, which at least partially comprises the flow channel. The pierceable septum is arranged on the pivotable arm. Preferably, the pivotable arm has at least partially the shape of a cylinder. The piercing surface of the septum is essentially parallel to at least a part of the pivotable arm. Hence, the pivotable arm may preferably be L-shaped. The arm is usually pivotable in the lateral direction of the cradle base, i.e. pivotable within the horizontal plane of the cradle base. These embodiments offer the advantage that any local stretching or compression of at least the inner piercing core of the septum or of the septum as a whole, which may be effected by piercing along an inclined piercing path may be compensated by the lateral movement of the pivotable arm. Furthermore, the pivotable arm may to a certain extend be pivotable with respect to the horizontal plane of the cradle base, i.e. the arm may be pivoted out of the horizontal plane of the cradle base, which may further lead to increased sealing behavior of the septum.

In some embodiments with a pivotable arm, the pivotable arm is pivotable in a lateral direction of the cradle base and/or pivotable out of a horizontal plane of the cradle base.

According to another aspect of this disclosure, a cradle for an infusion pump unit is provided, wherein the cradle has a proximal side and a distal side, the distal side having an infusion pump unit attachment structure for attaching an initially separate infusion pump unit. Furthermore, the cradle comprises a cradle base, a flow channel for a liquid drug and a pierceable septum, which covers an opening of the flow channel and seals the flow channel. The cradle further comprises a guide for providing a linear guiding path. The guide is arranged on the distal side of the cradle and surrounds the flow channel and the pierceable septum. The guide is movable along a piercing axis of the pierceable septum between an initial position and an operating position.

The piercing axis is typically transverse, particularly perpendicular, to a piercing surface of the septum. However, the piercing axis may also have a different angle.

Typically, the flow channel may be formed by a tubular part of the cradle base. Further, the guide may be at least partially movable along the flow channel. The guide is usually configured to provide a linear guiding path for connecting the cradle with an infusion pump unit via a transfer cannula of the infusion pump unit.

Thus, the guide guarantees that the septum is pierced along a linear guiding path, thereby providing a septum with an increased sealing behavior. Additionally, the septum may always accurately be pierced at the same position, as the guide provides a linear guiding path and avoids any deflection from the guiding path, in particular any deflection in a lateral direction of the cradle base. Thus, the septum is always pierced at the same position and multiple puncturing sites are avoided, which ultimately increases the tight sealing of the septum and allows to increase the number of coupling and decoupling events of the cradle and an infusion pump unit.

In further embodiments, the proximal side has a skin attachment member for releasable attachment of the cradle to the patient's skin as explained before and further below in the context of exemplary embodiments.

In some embodiments, in the initial position, the guide protrudes from the flow channel and the pierceable septum. Such an embodiment is advantageous, as the guide prevents in the initial position any piercing of the septum by an approaching cannula. Before the guide is moved in the operating position, the guide provides the linear puncturing path, which is preferably transverse, particularly perpendicular, to the piercing surface of the septum.

Typically, the guide may protrude 0.5 to 20 mm from the piercing surface of the septum in its initial position.

In some embodiments, the guide is tubular. Furthermore, the inner design of the guide is such that the guide surrounds and tightly fits around the flow channel and the pierceable septum.

In some embodiments, the guide is sliding movable between the initial position and the operating position. Thus, during the connection event of the cradle with an infusion pump unit, firstly the guide contacts the infusion pump unit, before the transfer cannula can penetrate and/or contact the septum. The guide then provides a linear guiding path, along which the transfer cannula is moved for penetrating the septum. When the user pushes the cradle and the infusion pump unit towards each other, the guide is moved between the initial position and the operating position in a sliding manner upon which the transfer cannula penetrates the septum.

In preferred embodiments, the guide comprises a cutout for enabling movement along at least parts of a curved or bent flow channel, in particular of a L-shaped flow channel.

According to a further aspect of this disclosure, the overall problem is solved by an infusion system comprising a cradle according to this disclosure as described in any of the embodiments above, and an infusion pump unit with a transfer cannula. The cradle and the infusion pump unit are releasably connectable, particularly via the pump unit attachment structure of the cradle and a corresponding respectively complementary cradle attachment structure of the infusion pump unit.

It is understood that in an initial state, the cradle and the infusion pump unit are not yet connected, while in the operating state, the cradle and the infusion pump unit are connected. That is, a fluid connection between the infusion pump unit and the flow channel of the cradle is established.

In some embodiments, the infusion system comprises a cradle with a guide as described in any of the embodiments above, wherein in the initial position, the guide prevents the transfer cannula of the infusion pump unit to pierce the septum before the septum and the transfer cannula are aligned in a predefined state. In the operating position, the transfer cannula can penetrate the septum substantially perpendicular to the piercing surface of the septum.

In some embodiments, the infusion system comprises a cradle with a guide as described in any of the embodiments above, wherein in the initial position, the piercing surface of the septum and the transfer cannula of the infusion pump unit are arranged substantially perpendicular to each other and/or the transfer cannula is arranged above a central area of the piercing surface of the septum. Thus, it is ensured that the septum is always pierced at the same position and consequently the occurrence of multiple puncturing sites is avoided in case of the infusion pump unit and the cradle being coupled and decoupled more than once. Therefore, the amount of coupling and decoupling events may be significantly increased, before leakage occurs or becomes a severe problem.

In preferred embodiments, the infusion system comprises a cradle with a guide as described in any of the embodiments above and the guide is configured such that any lateral relative movement between the cannula and the septum is prevented in the operating position.

In typical embodiments, the transfer cannula of the infusion pump unit is arranged within a recess, which preferably has a shape corresponding to the guide. The shape of the recess may also be tubular in some embodiments. Therefore, the guide may be arranged within the recess in the operating position. Such embodiments are particularly advantageous, as the guiding path provided by the guide is both linear and perpendicular with respect to the piercing surface of the septum.

According to a further aspect of this disclosure, a pierceable septum comprising a circumferential sealing ring, an inner piercing core and a deformable ribbon are provided. The sealing ring and the inner piercing core are connected by the deformable ribbon. The ribbon is configured such that the inner piercing core of the septum is movable with respect to the sealing ring of the septum. Preferably, the deformable ribbon is configured such that the inner piercing core of the septum may be movable in a lateral direction, i.e. towards a part of the sealing ring of the septum and/or tiltable with respect to a horizontal plane of the septum. It is understood that the horizontal plane of the septum is arranged perpendicular to the outer wall of the sealing ring and perpendicular to a piercing axis of the septum. On the one hand, the ribbon may thus enable movement of the inner piercing core of the pierceable septum and on the other hand enables a gas and/or liquid tight septum sealing the flow channel of the cradle. The septum according to this aspect may in particular be a septum according to an embodiment as discussed above in the context of a cradle and/or further below in the context of exemplary embodiments and the corresponding disclosure is also to be understood as referring to a septum as such.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
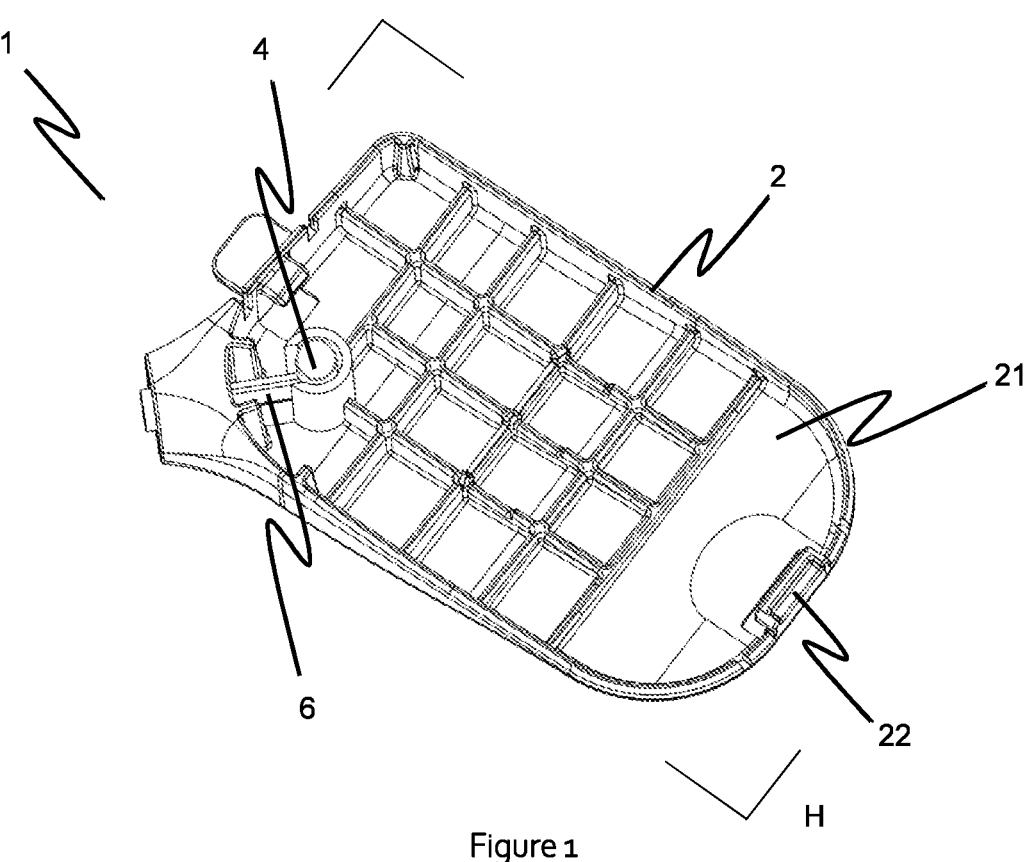
FIG. 1 shows a plan view of a cradle for an infusion pump unit according to a first embodiment.

An advantageous embodiment of a cradle for an infusion pump is shown in FIG. 1. The cradle 1 is shown in a top view from the distal side 21, wherein distal side 21 has infusion pump unit attachment structure 22 for attachment of an initially separate infusion pump unit. The cradle 1 comprises a cradle base 2 and pierceable septum 4, which covers an opening of a flow channel for a liquid drug. The pivotable arm 6 at least partially comprises the flow channel for a liquid drug (see FIG. 2). The pierceable septum 4 is movably mounted with respect to cradle base 2 via pivotable arm 6. The piercing surface of septum 4 is arranged essentially parallel to horizontal plane H of cradle base 2. As a result, at least parts of the flow channel are transverse to septum 4. As can be seen from FIG. 1, septum 4 is arranged on the pivotable arm 6 and thus seals the flow channel, which is at least partially arranged within pivotable arm 6. Pivotable arm 6 allows the septum or at least an inner core of the septum to be movable in a lateral direction of cradle base 2 and/or to be tiltable with respect to horizontal plane H of cradle base 2. Furthermore, pivotable arm 6 is pivotable in a lateral direction of cradle base 2. As readily understood, the lateral direction lies within horizontal plane H of the cradle base.

Figure 2:
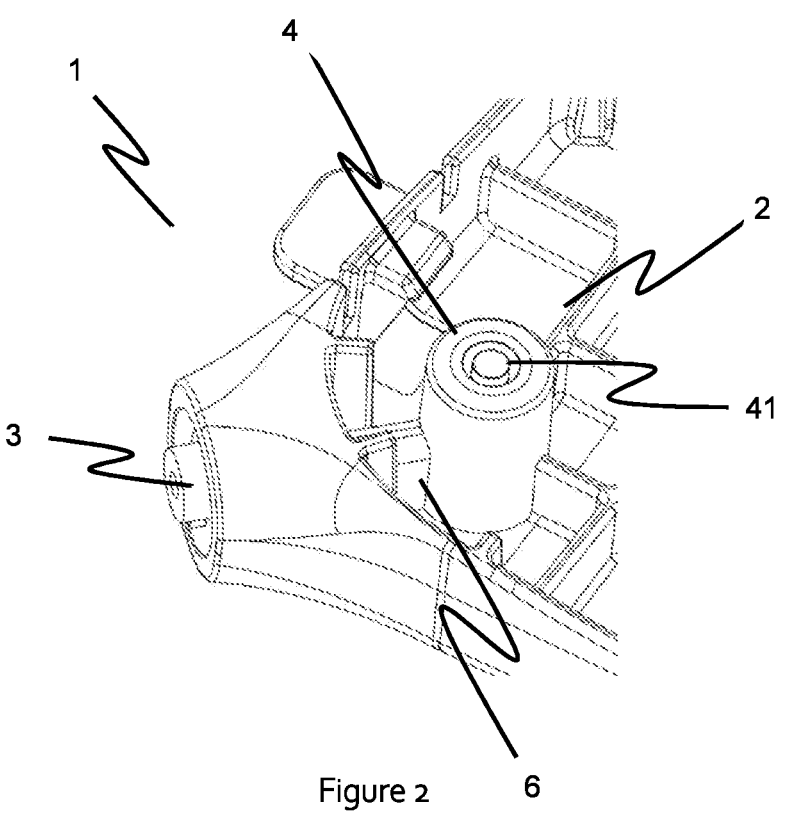
FIG. 2 shows a partial view of a cradle for an infusion pump unit according to another embodiment.

FIG. 2 shows a partial view of a cradle 1 according to another embodiment of this disclosure. As in FIG. 1, the cradle comprises cradle base 2, septum 4 and pivotable arm 6. Septum 4 additionally comprises inner piercing core 41, which is movably mounted to the cradle base. FIG. 2 further depicts flow channel 3, which is at least partially arranged within pivotable arm 6. The inner piercing core 41 of septum 4 may be individually movable with respect to pivotable arm 6 and cradle base 2.

Figure 3:
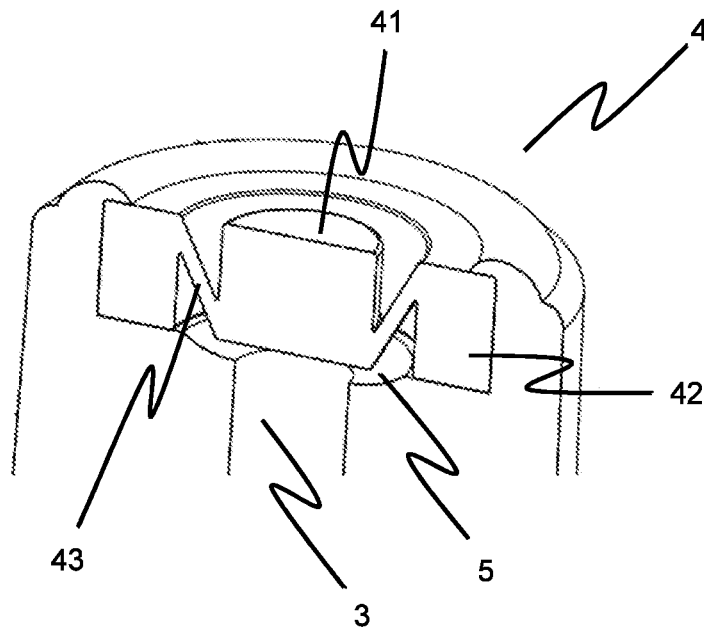
FIG. 3 shows a cross-sectional view of a section of a cradle for an infusion pump unit according to another embodiment.

FIG. 3 shows a detailed view of a septum 4 as used in a cradle for example according to FIG. 2, the septum comprising inner piercing core 41 and circumferential sealing ring 42, which are connected by deformable ribbon 43. As can be seen, ribbon 43 allows individual movement of the inner piercing core 41 when the circumferential sealing ring 42 is fixedly connected to either the cradle base or to the pivotable arm. The septum 4 further comprises an essentially flat piercing surface, which is pierced by a cannula upon establishing a fluid connection. Septum 4 covers the opening of flow channel 3 for a liquid drug and thus seals the flow channel. The septum shown in FIG. 3 is sealingly connected to the cradle base or to the pivotable arm, by crimping of circumferential sealing ring 42. Such embodiments are particularly advantageous, as the inner piercing core is movable both by tilting with respect to the horizontal plane of the cradle base, as well as by lateral movement, i.e. by varying the distance to circumferential sealing ring 42. Thus, if a cannula approaches inner piercing core 41 in a non-perpendicular manner, the inner piercing core tilts with respect to the horizontal plane of the cradle base upon contact with the cannula prior to the piercing event itself. As a result, inner piercing core 41 is always pierced in a transverse, preferably perpendicular manner with respect to the piercing surface. Furthermore, any pivoting movement of the piercing cannula during the piercing event can be compensated by lateral movement of the inner piercing core. Therefore, any deleterious stretching or compression effects within at least the inner piercing core of the septum are prevented or at least diminished. In addition, the cradle comprises stopper 5, which is configured to delimit a movement of the inner piercing core 41 of the septum in a vertical direction. Thus, when a cannula pierces septum 4, a vertical force exerted by the cannula on the septum pushes the inner piercing core 41 towards and potentially against stopper 5. As a result, the stopper may provide a counterforce to the piercing force of the cannula. As can be seen, the stopper is arranged below the lower surface of the inner piercing core 41 in a predetermined distance, such that a predefined vertical deflection of the septum is allowed. In this case, the stopper is simply designed as a broadening at the opening of the flow channel 3.

Figure 4:
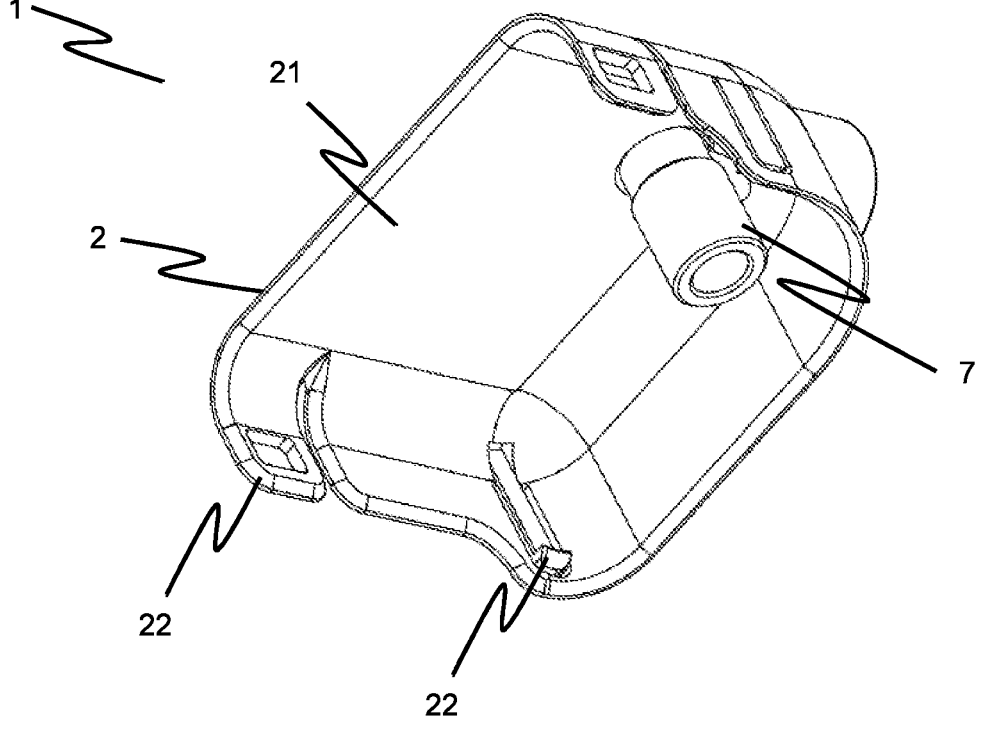
FIG. 4 shows a perspective view of a cradle for an infusion pump unit according to another embodiment.

FIG. 4 shows a cradle 1 for an infusion pump unit according to a further embodiment. Cradle 1 has a distal side 21 with infusion pump attachments 22 for attaching an initially separate infusion pump unit. Cradle 1 further comprises cradle base 2, a flow channel for a liquid drug (not shown, see FIG. 6) and a pierceable septum (not shown, see FIG. 6) covering and sealing the flow channel. Furthermore, cradle 1 comprises guide 7 for providing a linear guiding path. As can be readily seen from FIG. 4, guide 7 is arranged on distal side 21 of cradle base 2. Furthermore, guide 7 has a tubular shape and surrounds the flow channel as well as the pierceable septum. In the initial position shown in FIG. 4, guide 7 protrudes from the flow channel and the pierceable septum. As a consequence, when cradle 1 is connected to an infusion pump unit with a transfer cannula that is configured to protrude the pierceable septum of cradle 1, guide 7 is contacted with the infusion pump unit prior to the piercing event. In this position, the guide 7 prevents the piercing, as the protruding part of the guide is longer than the piercing part of the transfer cannula. When the piercing surface of the septum is essentially perpendicular to the transfer cannula of a infusion pump unit, the guide 7 is movable to an operating position upon which the cannula can pierce the septum.

Figure 5:
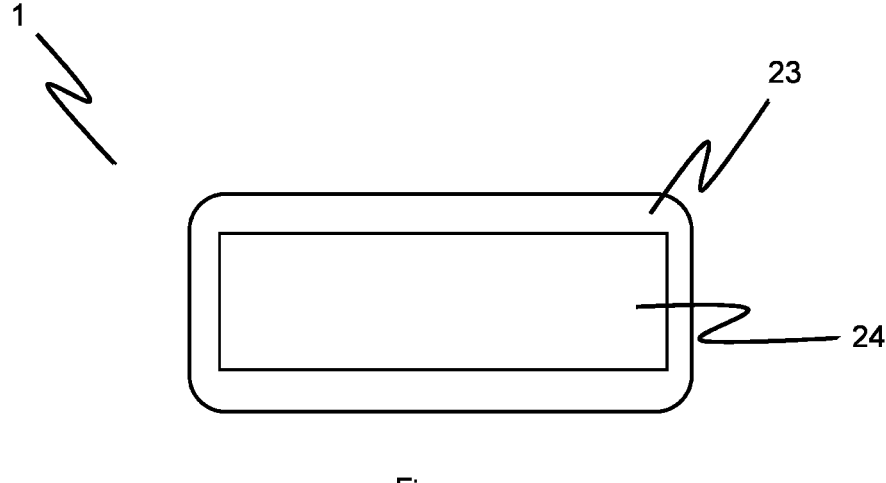
FIG. 5 shows a plan view of a cradle for an infusion pump unit according to another embodiment.

FIG. 5 shows a plan view of a cradle according to an advantageous embodiment. Cradle 1 is shown as a plan view on proximal side 23. For releasable attachment to the skin of the patient, the proximal side 23 has a skin attachment member 24 that is exemplarily realized as adhesive sheet.

Figure 6:
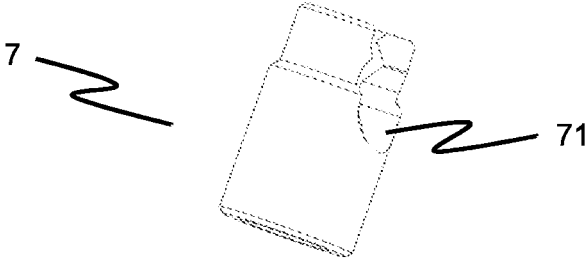
FIG. 6 shows a guide of a cradle for an infusion pump unit according to another embodiment.

FIG. 6 shows a detailed view of guide 7 as used in certain embodiments. As can be readily seen, guide 7 has a tubular shape and comprises a cutout 71, which enables sliding movement of the guide along at least parts of a curved, bent, in particular L-shaped flow channel (see below).

Figure 7:
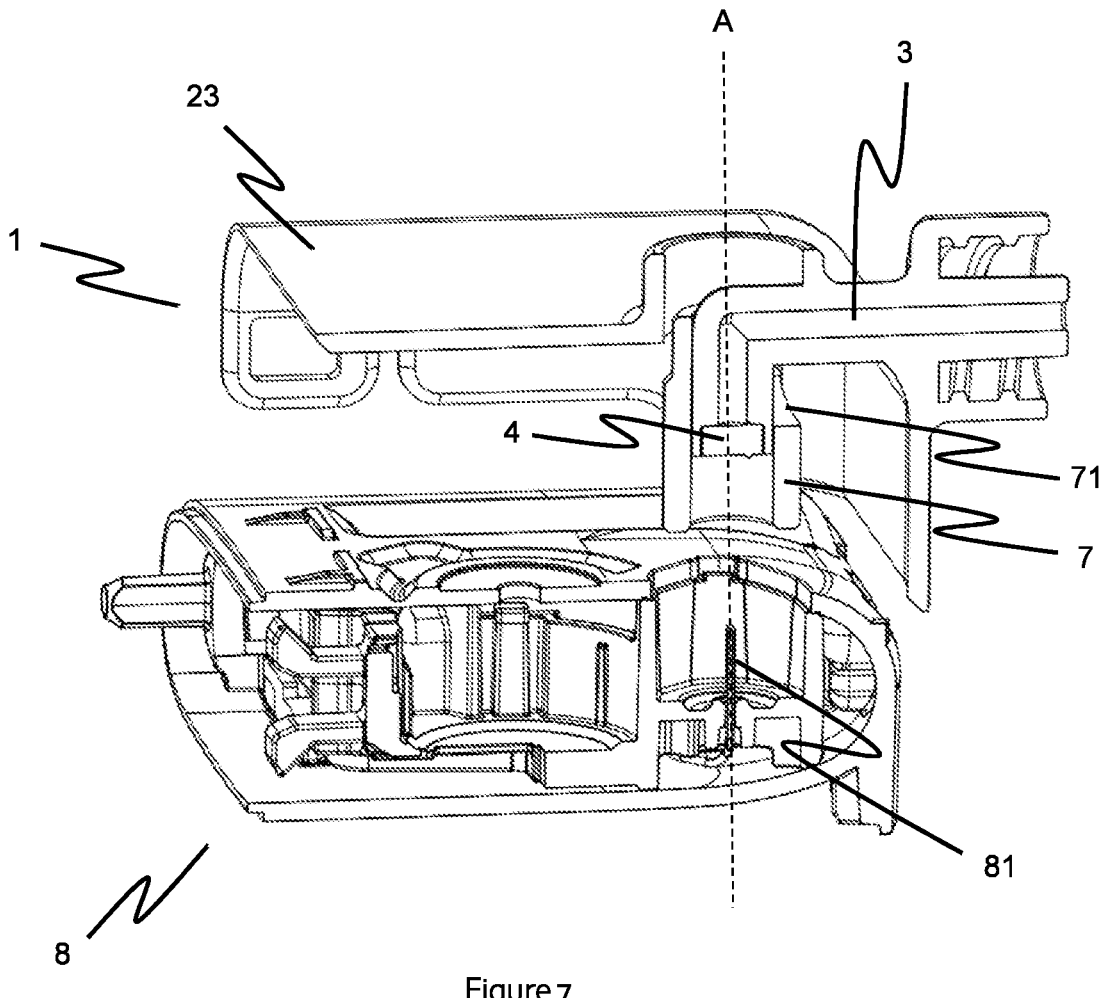
FIG. 7 shows an exploded perspective view of a cradle for an infusion pump unit according to another embodiment.

FIG. 7 shows a cradle 1 for an infusion pump unit 8, prior to their connection to form a connected infusion system. Cradle 1 comprises proximal side 23 and L-shaped flow channel 3 for a liquid drug. An opening of flow channel 3 is covered and sealed by pierceable septum 4. Cradle 1 further comprises guide 7 with cutout 71. The guide surrounds flow channel 3 and the pierceable septum 4. In the initial state shown, guide 7 protrudes from flow channel 3 and septum 4. The infusion pump unit comprises transfer cannula 81, which is configured to establish a fluid connection with flow channel 3 of cradle 1 upon piercing of septum 4. The guide is configured such that it provides a linear guiding path along piercing axis A.

Figures 8A, 8B, 8C:
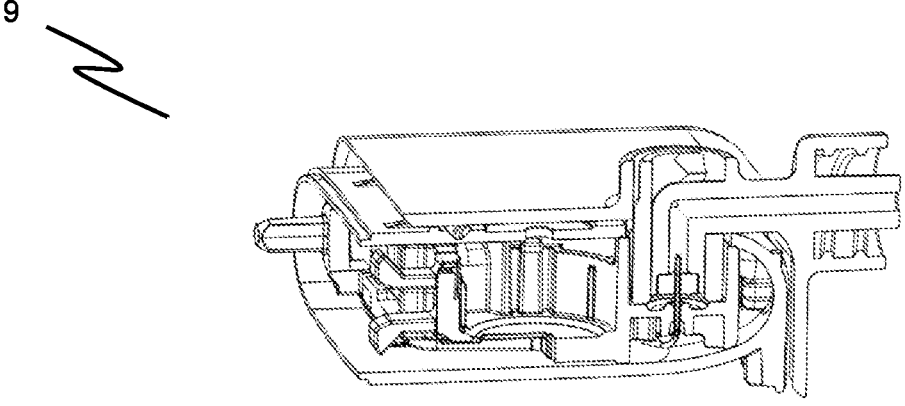
FIGS. 8a to 8c show views of a cradle for an infusion pump unit according to another embodiment in different stages of establishing a connection with an infusion pump unit.

FIGS. 8a to 8c show the connection of a cradle 1 and an infusion pump unit 8 to form a connected infusion system 9. FIG. 8a shows the initial position of cradle 1, in which guide 7 surrounding L-shaped flow channel 3, protrudes from flow channel 3 and pierceable septum 4. As can be readily seen, transfer cannula 81 of the infusion pump unit 8 is arranged in a recess whose shape corresponds to the shape of guide 7. It is understood that the guide 7 shown in FIG. 8a guarantees that the septum is pierced transversely to its piercing surface, in particular perpendicularly.

When cradle 1 and infusion pump unit 8 are pushed towards each other, guide 7 is inserted into the recess of the infusion pump unit. In the intermediate state shown in FIG. 8b, the guide has not yet moved along the flow channel, however it is in contact with the infusion pump unit 8. Due to the fact that guide 7 protrudes from pierceable septum 4 and flow channel 3, the guide prevents piercing of septum 4 before a straight, transverse, in particular perpendicular guiding path with respect to the piercing surface of the septum along piercing axis A is established.

When cradle 1 and infusion pump unit 8 are further pushed together, guide 7 is moved into the operating position shown in FIG. 8c. Thereby, guide 7 is moved relatively to septum 4 and flow channel 3, such that the protruding part is continuously decreased upon which transfer cannula 81 can penetrate septum 4 and establish a fluid connection between the infusion pump unit and flow channel 3 of cradle 1. Cutout 71 of guide 7 ensures that the L-shape of flow channel 3 does not prevent movement of the guide along flow channel 3. As a consequence, the infusion system can be designed in a relatively flat and discreet manner. It is understood that the guide further guarantees in the embodiment shown that the septum is always pierced at the same position and that thus multiple puncturing sites are avoided.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF DESIGNATIONS 1 cradle
2 cradle base
21 distal side
22 infusion pump unit attachment structure
23 proximal side
24 skin attachment member
3 flow channel
4 septum
41 inner piercing core
42 sealing ring
43 ribbon
5 stopper
6 pivotable arm
7 guide
8 infusion pump unit
81 transfer cannula
9 infusion system

What is claimed is:

1. A cradle for use with an infusion pump, the cradle comprising:
a proximal side and a distal side, the distal side having an infusion pump attachment structure configured for attaching an initially separate infusion pump;
a cradle base;
a flow channel for a liquid drug; and
a pierceable septum covering an opening of the flow channel and sealing the flow channel, the pierceable septum having an inner piercing core that is movably mounted with respect to the cradle base, wherein the pierceable septum as a whole is movable in a lateral direction of the cradle base and/or tiltable with respect to a horizontal plane of the cradle base.

2. The cradle according to claim 1, wherein the pierceable septum is sealingly connected to the cradle base by clamping or crimping.

3. The cradle according to claim 1, wherein at least the inner piercing core is movable in a lateral direction of the cradle base and/or tiltable with respect to a horizontal plane (H) of the cradle base.

4. The cradle according to claim 1, wherein the pierceable septum comprises a circumferential sealing ring, the inner piercing core and a deformable ribbon, wherein the sealing ring and the inner piercing core are circumferentially connected by the deformable ribbon, whereby the inner piercing core is pivotable relative to the sealing ring and pivotable relative to the cradle base.

5. The cradle according to claim 4, further comprising a stopper configured to delimit a movement of the inner piercing core of the pierceable septum.

6. The cradle according to claim 4, further comprising a gap disposed between the sealing ring and the inner piercing core.

7. The cradle according to claim 1, further comprising a pivotable arm, wherein the flow channel is at least partly disposed in the pivotable arm, and wherein the pierceable septum is arranged on the pivotable arm and a piercing surface of the pierceable septum is essentially parallel to at least a part of the pivotable arm.

8. The cradle according to claim 7, wherein the pivotable arm is pivotable in a lateral direction of the cradle base and/or pivotable out of a horizontal plane of the cradle base.

9. The cradle according to claim 1, wherein the flow channel extends in a direction substantially parallel to a piercing surface of the pierceable septum.

10. An infusion system, comprising:
the cradle according to claim 1; and
an infusion pump with a transfer cannula, wherein the cradle and the infusion pump are releasably connectable.

11. The cradle for use with an infusion pump according to claim 1, wherein the flow channel is at least partially arranged within a pivotable arm and the inner piercing core is individually moveable with respect to the pivotable arm and the cradle base.

12. The cradle for use with an infusion pump according to claim 11, wherein the pivotable arm is L-shaped.

13. The cradle for use with an infusion pump according to claim 1, wherein a periphery of the pierceable septum is sealingly connected to the cradle base.

14. A cradle for use with an infusion pump having a transfer cannula, the cradle comprising: a proximal side and a distal side, the distal side having an infusion pump attachment structure configured for attaching an initially separate infusion pump; a cradle base; a flow channel for a liquid drug; and a pierceable septum covering an opening of the flow channel and sealing the flow channel, the pierceable septum having an inner piercing core that is movably mounted with respect to the cradle base, wherein the pierceable septum as a whole is movable in a lateral direction of the cradle base and/or tiltable with respect to a horizontal plane of the cradle base; a guide arranged on the distal side of the cradle and configured for providing a linear guiding path along a piercing axis (A) of the pierceable septum; wherein the guide surrounds the flow channel and the pierceable septum and the guide guides the flow channel and pierceable septum along the piercing axis (A); wherein the guide is movable along the piercing axis (A) toward the transfer cannula and wherein the guide has a complementary shape to the flow channel and/or the pierceable septum.

15. The cradle according to claim 14, wherein in an initial position the guide protrudes from the flow channel and the pierceable septum.

16. The cradle according to claim 14, wherein the guide is tubular.

17. The cradle according to claim 14, wherein the guide is slidable between an initial position and an operating position.

18. An infusion system, comprising:
the cradle according to claim 14; and
an infusion pump with a transfer cannula, wherein the cradle and the infusion pump are releasably connectable.

19. The infusion system according to claim 18, wherein in an initial position, the guide prevents the transfer cannula of the infusion pump to pierce the pierceable septum before the pierceable septum and the transfer cannula are aligned in a predefined state, and wherein in an operating position, the transfer cannula can penetrate the pierceable septum substantially perpendicular to a piercing surface of the pierceable septum.

20. The infusion system according to claim 18, wherein in an initial position, a piercing surface of the pierceable septum and the transfer cannula of the infusion pump unit are arranged substantially perpendicular to each other and/or the transfer cannula is arranged above a central area of a piercing surface of the pierceable septum.

21. The infusion system according to claim 18, wherein the guide is configured such that any lateral relative movement between the transfer cannula and the pierceable septum is prevented in an operating position.

22. The cradle for use with an infusion pump according to claim 14, wherein the flow channel comprises an L-shaped arm.

23. A cradle for use with an infusion pump, the cradle comprising: a proximal side and a distal side, the distal side having an infusion pump attachment structure configured for attaching an initially separate infusion pump; a cradle base; a flow channel for a liquid drug, the flow channel comprising a pivotable L-shaped arm; and a pierceable septum covering an opening of the flow channel and sealing the flow channel, the pierceable septum having an inner piercing core that is pivotably mounted with respect to the cradle base, wherein the pierceable septum as a whole is movable in a lateral direction of the cradle base and/or tiltable with respect to a horizontal plane of the cradle base.

24. The cradle for use with an infusion pump according to claim 23, wherein the inner piercing core is individually moveable with respect to the pivotable L-shaped arm and the cradle base.

25. A cradle for use with an infusion pump having a transfer cannula, the cradle comprising: a proximal side and a distal side, the distal side having an infusion pump attachment structure configured for attaching an initially separate infusion pump; a cradle base; a flow channel for a liquid drug; and a pierceable septum covering an opening of the flow channel and sealing the flow channel, the pierceable septum having an inner piercing core that is movably mounted with respect to the cradle base, wherein the pierceable septum as a whole is movable in a lateral direction of the cradle base and/or tiltable with respect to a horizontal plane of the cradle base; a guide arranged on the distal side of the cradle and configured for providing a linear guiding path along a piercing axis (A) of the pierceable septum; wherein the guide surrounds the flow channel and the pierceable septum and the guide guides the flow channel and pierceable septum along the piercing axis (A); wherein the guide is slidable along the piercing axis (A) toward the transfer cannula; and wherein the guide has a complementary shape to the flow channel and/or the pierceable septum.

* * * * *